United States Patent [19]
Lewis

[11] Patent Number: 5,735,813
[45] Date of Patent: Apr. 7, 1998

[54] DOUBLE LUMEN INTRODUCING NEEDLE

[75] Inventor: Ronald L. Lewis, Glen Mills, Pa.

[73] Assignee: Danron, Inc., Media, Pa.

[21] Appl. No.: 735,470

[22] Filed: Oct. 23, 1996

[51] Int. Cl.$^6$ ........................................ A61M 5/00
[52] U.S. Cl. ........................ 604/43; 604/164; 604/280
[58] Field of Search ........................... 604/43–45, 272, 604/280, 284, 164

[56] References Cited

U.S. PATENT DOCUMENTS

| | | |
|---|---|---|
| 519,635 | 5/1894 | Kregel . |
| 2,564,977 | 8/1951 | Hu . |
| 4,098,275 | 7/1978 | Consalvo . |
| 4,099,528 | 7/1978 | Sorenson et al. . |
| 4,134,402 | 1/1979 | Mahurkar . |
| 4,203,436 | 5/1980 | Grimsrud . |
| 4,403,983 | 9/1983 | Edelman et al. . |
| 4,493,696 | 1/1985 | Uldall . |
| 4,619,643 | 10/1986 | Bai . |
| 4,626,240 | 12/1986 | Edelman et al. . |
| 4,675,004 | 6/1987 | Hadford et al. . |
| 4,682,978 | 7/1987 | Martin . |
| 4,935,008 | 6/1990 | Lewis, Jr. . |

*Primary Examiner*—John D. Yasko
*Attorney, Agent, or Firm*—Panitch Schwarze Jacobs & Nadel, P.C.

[57] ABSTRACT

A double lumen introducing needle includes a hub having diametrically opposing mounting and distal ends connected by an at least substantially straight axial passageway. A side passageway branches from a junction between the ends and extends away from the junction and the distal end of the hub at an acute angle to the reminder of the axial passageway and terminates in a separate side port. A first, inner lumen extends continuously and unbrokenly from the side passageway through the junction along the axial passageway and projects outwardly from the distal end of the hub. The open end of the inner lumen in the side port is fluidly isolated by a seal from the axial passageway. An outer tube is mounted to the hub at the distal end. The outer tube projects outwardly from the distal end around the first lumen and defines at least part of a second, outer lumen surrounding the first, inner lumen. The outer lumen is fluidly coupled with a syringe at the mounting end of the hub through the axial passageway. The hub can be provided with a releasable coupling at the mounting end to releasably engage a conventional syringe, or at the distal end to releasably engage a conventional releasable needle, at both ends, or at neither end in the case of a disposable needle and syringe. The needle can be used to insert flexible wire members like guidewires or electrodes into blood vessels.

25 Claims, 3 Drawing Sheets

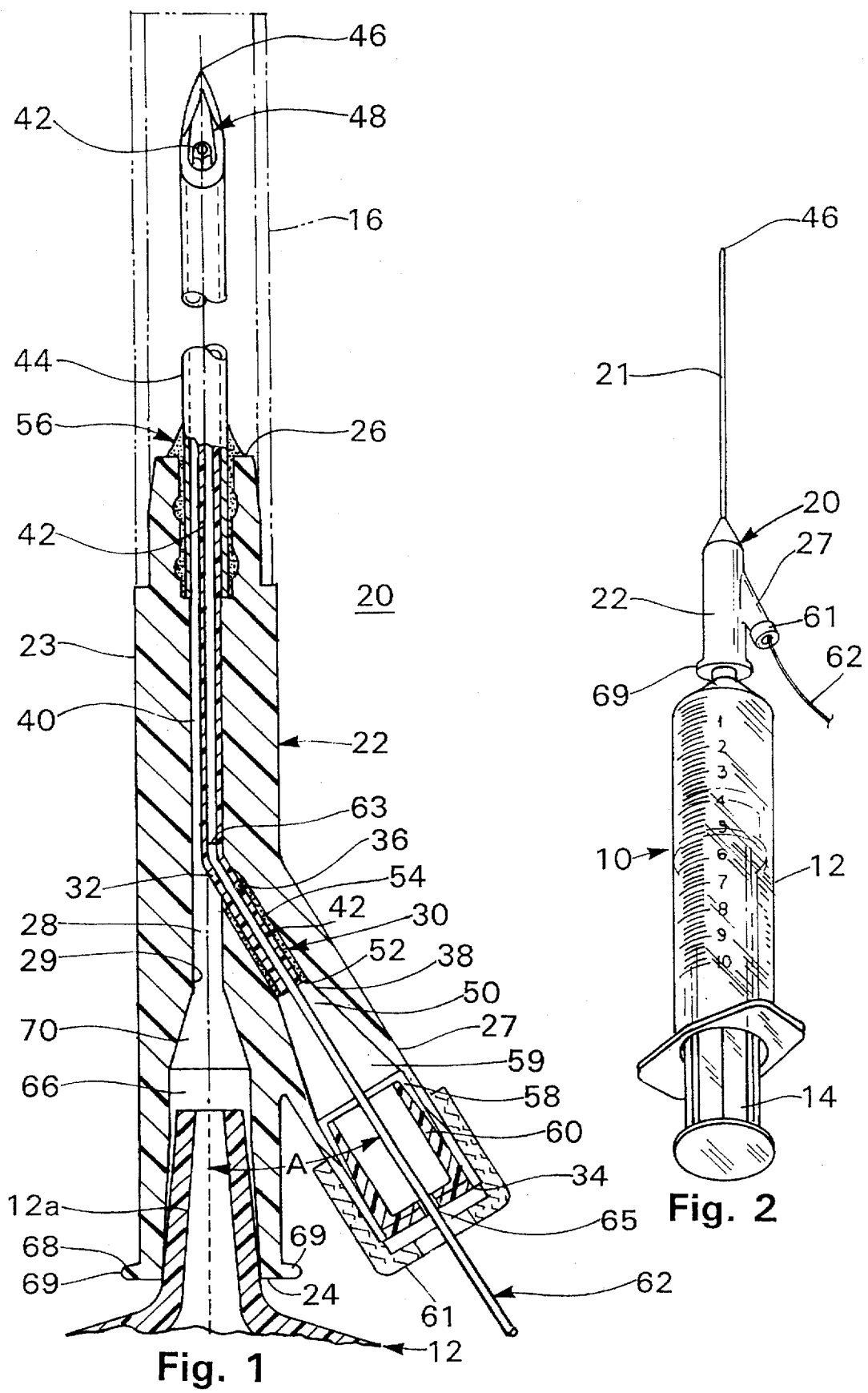

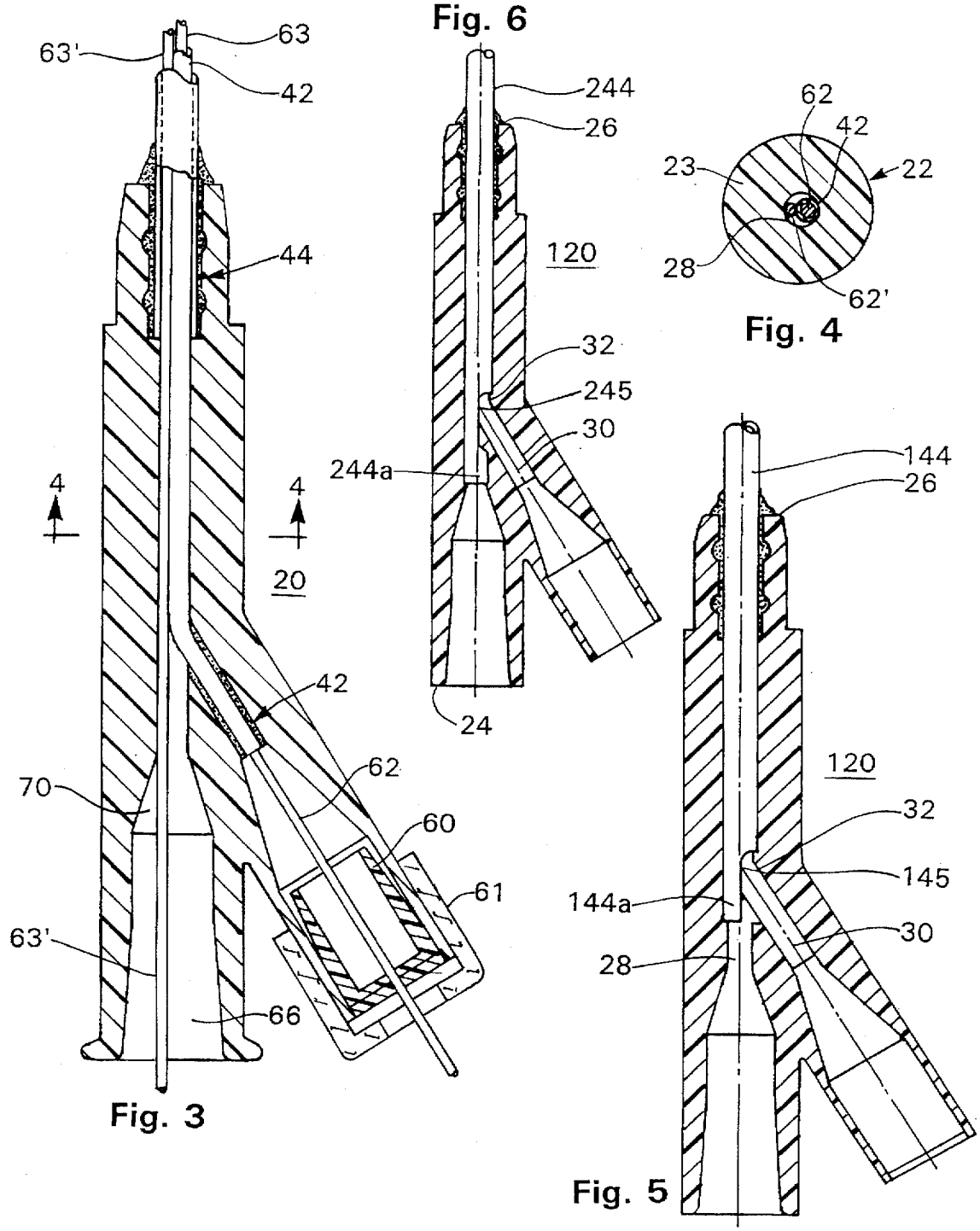

DOUBLE LUMEN INTRODUCING NEEDLE

FIELD OF THE INVENTION

The disclosed invention relates to medical needles, and more particularly to introducing needles, i.e., needles used to "introduce" guidewires or other thin flexible members into human blood vessels during various medical procedures. The invention also relates to a method for introducing thin flexible members into human blood vessels using the disclosed apparatus of the invention.

BACKGROUND OF THE INVENTION

In the practice of modern medicine, it often is necessary to insert one or more guidewires directly into human blood vessels. These guidewires may be used as "pilots" for subsequent insertion of various types of catheters, wherein the catheter is concentrically inserted over a guidewire previously inserted into a blood vessel, after which the guidewire is withdrawn, leaving the catheter positioned within the blood vessel. In cardiac medicine, guidewires also may be inserted into a blood vessel and thereafter "worked" through the vessel toward a patient's heart in order to clear blockages or implant permanent cardiac pacemakers, among other things.

Depending upon the particular medical procedure performed, guidewires may be inserted into either veins or arteries, although, the present invention is described in terms of the introduction of guidewires into veins, it should be understood that the invention is not limited to use in veins and may, under appropriate circumstances, be used for procedures involving insertion of guidewires or other thin flexible members into arteries.

Conventional introducing needles resemble standard "hypodermic" needles in that they have only a single bore or "lumen". The principal difference between conventional introducing needles and hypodermic needles is that the lumen of an introducing needle generally has a larger internal diameter in order to accommodate passage of a guidewire. A guidewire is introduced into a vein using a single lumen needle by first puncturing the vein with the sharpened tip of the needle and thereafter drawing back on the plunger of the syringe barrel attached to the needle so that a "flash" of blood is obtained. This ensures that the vein his been completely punctured and the needle tip is properly positioned within the vein. The syringe barrel then is disengaged and removed from the needle and the guidewire is inserted into the exposed hub of needle and thereafter through the single lumen of the needle and into the vein.

Single lumen introducing needles have several disadvantages. As described above, after a vein is punctured with a single lumen needle and a flash of blood is drawn, the syringe barrel must be disengaged and removed from the needle before insertion of the guidewire can be accomplished. The process of disengaging and removing the syringe barrel from the needle necessarily involves pulling, twisting, or turning the syringe barrel in relation to the needle. This may cause substantial manipulation of the needle while it is in place within the vein, which may result in trauma to the vein and unnecessary discomfort to the patient. Moreover, this manipulation of the needle may result in its movement from the initial puncture site, thereby preventing free passage of the guidewire into the vein and requiring that the vein be repunctured, with further increased risk of trauma to the vein and discomfort to the patient.

Another disadvantage of single lumen introducing needles is that, when performing procedures which require insertion of two guidewires into a vein, two separate introducing needles must be used. Each needle has only a single lumen that will allow passage of only one guidewire through the needle and its puncture location. As a result, when two guidewires are required, it is necessary to puncture the particular vein at two separate locations. This procedure significantly increases the risk of patient discomfort and trauma to the vein, particularly when the two separate puncture locations are in close proximity to each other. Another disadvantage of single lumen needles is that with placement of guidewires there is an obligatory need to expose healthcare providers to blood and bodily fluids, many of which contain pathogens, which may cause illness to the provider.

Double lumen needles are also known. The most common design is created by introducing a central dividing wall down the length of an otherwise cylindrical needle shaft to create two side-by-side parallel lumens of generally hemispheric cross-sectional shapes. Applicant's own U.S. Pat. No. 4,935,008 discloses such a double lumen configuration in an introducing needle. While simple in concept, such needles have proven to be very difficult and expensive to reliably manufacture.

Concentric double lumen cannulas are also known for hemo-dialysis. U.S. Pat. Nos. 4,099,523 and 4,493,696 each disclose cannulas having two concentrically positioned lumens for hemodialysis treatment. However, the originally simple construction of each device is complicated by the provision of some type of movable seal between the inner and outer lumens. In each instance, the inner lumen of the device extends axially in a straight line through the device including a branching hub provided at a mounting end of the device.

OBJECTS OF THE INVENTION

It is an object of this invention to provide an introducing needle that substantially reduces the amount of manipulation applied to the needle during insertion of a guidewire into a vein punctured by the needle.

It is a further object of this invention to provide a double lumen introducing needle that eliminates the need to disengage and remove the syringe barrel from the needle to accomplish insertion of a guidewire into a vein punctured by the needle.

It is yet a further object of this invention to provide a double lumen introducing needle that enables two guidewires to be inserted into a vein through the single puncture location of the needle.

It is still a further object of this invention to provide a double lumen introducing needle which is more easily and inexpensively fabricated than a needle having side-by-side parallel lumens.

It is another object of this invention to provide a method for inserting a guidewire into a vein wherein the amount of manipulation applied to the introducing needle during the insertion procedure is substantially reduced.

It is yet another object of this invention to provide a method for inserting a guidewire into a vein without having to disengage and remove the syringe barrel from the introducing needle during the insertion procedure.

It is still another object of this invention to provide a method for inserting two guidewires through a single introducing needle and into a vein at a single puncture location.

It is still another object of this invention to provide a method of placing a guidewire into a blood vessel or hollow cavity while minimizing exposure to potentially life threatening pathogens.

These and other objects of the invention will be better appreciated after the reading the succeeding description of the invention in conjunction with the accompanying drawings.

SUMMARY OF THE INVENTION

In one aspect, the invention is a double lumen introducing needle comprising: a hub having a mounting end and an distal end axially opposing the mounting end, an at least substantially straight axial passageway extending through the hub between the mounting and distal ends and a side passageway branching from a junction with the axial passageway in the hub and extending away from the junction and the distal end of the hub at an acute angle to the axial passageway extending from the junction to the mounting end, the side passageway terminating in a separate, side port of the hub; an inner lumen extending continuously and unbrokenly from the side passageway, through the junction, along the main passageway between the junction and the distal end of the hub and projecting outwardly from the distal end of the hub, the inner lumen having a first open end located within the hub and fluidly isolated from the axial passageway; and sidewalls of the hub defining the axial passageway surrounding an outer lumen extending between the mounting end and distal end of the hub and surrounding the inner lumen within the axial passageway.

The disclosed invention also comprises a method for inserting a flexible wire into a vein using the aforesaid double lumen introducing needle.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is a perspective view of a first embodiment of the apparatus of the invention, co-joined with the barrel of a standard syringe;

FIG. 2 is a longitudinally sectioned view of the first embodiment apparatus of FIG. 1;

FIG. 3 is cross-section similar to FIG. 2 depicting two flexible wire members being fed through the needle;

FIG. 4 is a cross-section taken along lines 4—4 in FIG. 3;

FIG. 5 is a second embodiment needle according to the present invention;

FIG. 6 depicts another type of outer tube which can be used in needles of the present invention.

DETAILED DESCRIPTION OF PREFERRED EMBODIMENTS

Figure 7:
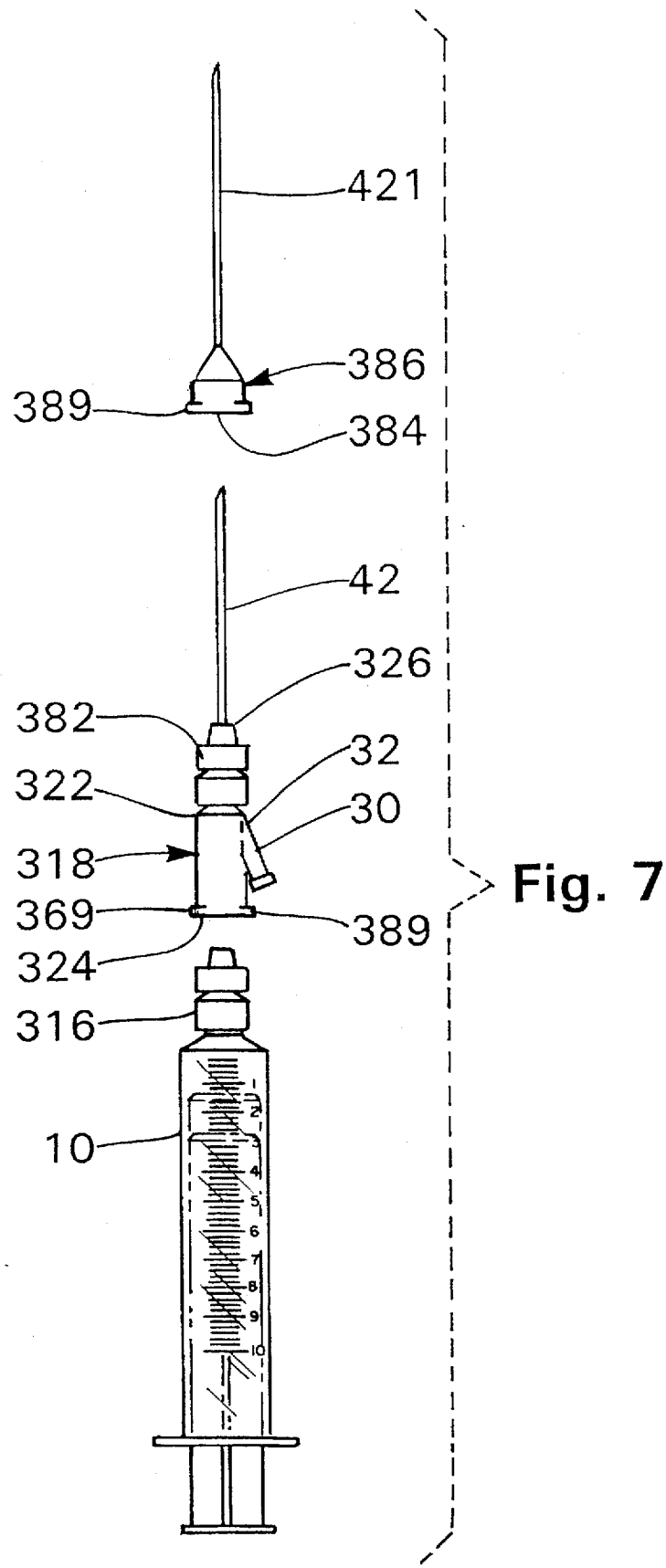
FIG. 7 is a third embodiment needle according to the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the and designated parts thereof. The terminology includes the words above specifically mentioned, derivatives thereof and words of similar import.

FIG. 1 depicts a standard syringe 10 having a barrel 12 and piston or plunger 14 and a double lumen introducing needle of the present invention indicated generally at 20. Referring now to FIG. 2, the needle 20 comprises a hub 22 with a straight body portion 23 having a mounting end 24 and a distal end 26 axially opposing the mounting end 24, which define axially opposing ends of the hub 22. A shank 21 projects from the distal end 26. An at least substantially straight, axial passageway 28 extends axially entirely through the hub 22 between the mounting and distal ends 24 and 26. The hub 22 further includes a sidearm portion 27 branching from the straight body portion 23. A side passageway 30 branches from a junction 32 with the axial passageway 28 in the straight body portion 23 of hub 20. Side passageway 30 extends away from the junction 32 and the distal end 26 of the hub 22, through the sidearm portion 27 at an acute angle "A" to the portion 28a of the axial passageway 28 extending from the junction 32 to the mounting end 24. The side passageway 30 terminates in a side port 34 of the hub 22.

A first, inner lumen 36 extends continuously and unbrokenly from the side passageway 30 through the junction 32 along the portion 28b of the axial passageway between the junction 32 and distal end 26 of the hub 22 and projects outwardly from the distal end of the hub 22. The first lumen 36 has a first open end 50 located within the hub 20, which end is fluidly isolated from the axial passageway 28. Sidewalls 29 of the hub 22 defining the axial passageway 28 surround a second, outer lumen 40 of needle 20. The second lumen 40 extends between the mounting end 24 and distal end 26 of the hub 20 and surrounds the first lumen 36 within the axial passageway 28 between junction 32 and distal end 26.

More particularly, the first lumen 36 is defined by the hollow interior of a first, inner tube 42 which extends continuously and unbrokenly from the side passageway 30 through the junction 32, along the portion 28b of the main passageway 28 between the junction 32 and the distal end 26 of the hub and projects outwardly from that distal end 26. A second, outer tube 44 is provided extending from the distal end of the axial passageway 28 away from the hub 22 and extends entirely around the first tube 42 extending from the hub. The second tube 44 has a hollow interior which defines at least a portion of the second, outer lumen 40 of the needle 20 surrounding the first tube 42 and first, inner lumen 36. The second tube 44 is fluidly coupled with the mounting end 24 of the hub 22 through the axial passageway 28. The remainder of the second, outer lumen 40 is defined by the sidewalls 29 of the axial passageway 28, which are exposed in the passageway 28 beyond the end of the second tube 44 terminating within the hub 22.

The second tube 44 is relatively rigid and preferably more rigid than the inner tube 42 and forms the shank 21 of needle 20. Second tube 44 preferably has a bevel 48 which, at least in part, defines a point 46 at the free distal tip of tube 44.

The first, inner lumen 36 has a proximal end, the first open end 50, which is located within the hub 22 and is fluidly isolated from the main axial passageway 28. More particularly, the proximal end 50 of the first, inner lumen 36 is defined, in part, by a proximal open end 52 of the first tube 42, which preferably terminates along the side passageway 30, and, in part, by a portion of the side passageway which extends beyond the end of the first tube 42 and defines the side port 34. The first tube 42 has an outer tubular wall 43 which is preferably sealed with the side passageway 30 by suitable means such as a bond layer 54 circumscribing the first tube 42 between its outer tubular surface and the walls defining the side passageway 30. The bond layer may be a solvent bond if appropriate plastic materials are selected for the first tube 42 and hub 22. Also, an adhesive material bond, a thermal bond or an ultrasound bond may alternatively be provided or preferred, depending upon the nature of the material of the first tube 42 and hub 22. Alternatively, a pressure/friction seal may be created between the distal end of a rigid tube 42 and the side passageway by close dimensional tolerances or a seal member such as an O-ring can be introduced between such first tube 42 and the sidewalls of side passageway 30. A bond layer 56 between the outer surface of the second tube 44 and the side walls 29 defining the axial passageway 28 preferably also secures the proximal end of the second tube 44 within the distal end 26 of the hub 22. However, second tube 44 can be fixedly secured to hub 22 in any suitable manner including pressure/friction engagement, post-insertion melting of the hub around tube 44, etc.

The diameter of the first tube 42 is sufficiently great to at least allow passage of a flexible wire member 62 like a guidewire of the type commonly used in various medical procedures, which is indicated in FIGS. 1-4. The acute angle A between the axial passageway 28 and side passageway 30 is selected to enable the physician to comfortably control the needle 20 through the syringe 10 attached to the needle 20 while simultaneously manipulating member 62 through the first lumen 36 and allow that member 62 to pass through the first tube 42 particularly through junction 32. The acute angle A may be from a minimum of 10° to a maximum of 45°.

Mounting end 24 of the hub 20 preferably is configured as a connector releasably matable with the distal tip 12a of syringe 10. For example, the axial passageway 28 terminates at the mounting end 24 of the hub 22 in an enlarged, tapered opening 66, matingly matching the taper of the distal tip 12a of syringe 10. More particularly, the opening 66 is preferably provided with a standard Luer taper of about 0.06 in./in. A radially outwardly projecting, Luer-type connection flange is provided on the hub 22 at the mounting end 24 around the enlarged tapered opening 66 in the form of a pair of diametrically opposed dogs 69. The hub 20 with Luer taper and flange 68 can be releasably mounted on the tip of a standard, slip-fit, friction engagement syringe barrel as shown or one equipped with a standard Luer-type receiver releasable connector.

A second more severely tapered portion 70 of the axial passageway 28 is provided between the junction 22 and enlarged tapered opening 66 at the mounting end 24 of the axial passageway 28 to facilitate the insertion of a guidewire or other solid member into the axial passageway 28 and second lumen 40 as will be subsequently described.

Side passageway 30 is also preferably provided with an enlarged opening 58 at its terminus in side port 34 for receipt of a plug-type closure 60. If desired, a stopper seal cap 61 with central opening can be provided over the closure 60 to assure its retention in the enlarged opening 58. If desired, other types of closures can be used including cap-type closures. In such cases, it may be unnecessary to provide an enlarged opening at the terminal end of the side passageway 30. In either event, a portion 59 of the side passageway 30 preferably is tapered to facilitate the insertion of the leading end 63 of flexible wire member 62 into the first lumen 36 and first tube 42.

Flexible wire member 62 may be a conventional guidewire such as a floppy straight or "J" wire with the "J" used as the leading end 63. Alternatively, flexible wire member 62 can be a cardiac lead, with an exposed electrode tip at the leading end 63. The leading end 63 of flexible wire member 62 is preferably preinserted into the first, inner lumen 36, preferably through a preformed slit opening 65 through a closure 60. A guidewire would be used with needle 20 to facilitate placement of catheters into blood vessels. The invention is, however, not limited to placing guidewires for vascular catheter placement. The guidewire 62 may be used with needle 20 to place a catheter into any hollow body cavity for purposes of draining that cavity or delivering specific therapeutic or diagnostic agents, i.e. draining abscesses, cysts and natural body cavities or instilling radiocontrast(s). The guidewire, once placed in a vein or artery, may be used for pacemaker lead insertion in which the hollow pacemaker lead is passed over the wire as a guide.

The hub 22 is preferably molded from an otherwise suitable plastic material acceptable for such use. One such material is StyrB1CP (K-Resin KR03) from the Plastics division of Phillips Chemical Co., Pasadena, Tex. The first, inner tube 42 is preferably formed from a compatible plastic material i.e. a medical grade polyvinylchloride which can be bonded with the hub 20 using an epoxy resin such as 186 M-T UV cure epoxy resin of Dymax, Inc. Torrington, Conn. Other, compatible, commercially available medical grade bonding material can also be used. The second tube 44, which forms the shank 21 of the needle 20, is preferably stainless steel and is of a gauge sufficiently large to permit the passage of two flexible wire members therethrough, with the first, inner tube. Suggestedly the second, outer tube 44 is at least 18 gauge. The maximum diameter of the outer tube 44 can be any diameter suitable for the ultimate use of device 20 but is suggestedly no more than about 15 gauge for use as an introducing needle. The same epoxy material can be used to bond the outer, stainless steel tube to the hub. The flexible wire member 62 can be marked at regular intervals, for example 5 cm lengths and can be variable in total length depending on the indication for the procedure.

The method of using the needle 20 of the present invention will now be described with reference to a right-handed physician inserting a guidewire type flexible member 62 into a vein. It will be understood that in preparing to insert the flexible wire member 62 into a vein, the needle 20 of the present invention is positioned in accordance with accepted medical procedures so that the bevel 48 faces up, i.e., away from the vein to be punctured and toward the physician. When the needle 20 is so oriented, the side arm portion 27 and side passageway 30 will project from the right-hand side of the straight body portion 23 of hub 22 during puncture of the vein. The leading end 63 of wire member 62 is preferably preinserted through closure 60 and into the inner tube 42 defining first lumen 36, through closure 64 and along side passageway 30 and first tube 42, preferably at least through the bend at junction 32 and into the main, axial passageway 28. After vein puncture, the piston 14 is drawn back in the syringe barrel 12 to obtain a "flash" of blood thereby indicating that the open end of the needle shank 21 defined by the bevel 48 has completely punctured the vein and is properly positioned within its interior cavity. After the "flash" of blood is drawn, the right-handed doctor grasps the syringe barrel 12 and needle 20 securely in his left hand so that the needle 10 maintains a fixed position with respect to the punctured vein. At the same time, the right-handed doctor grasps the flexible wire member 62 and feeds it through the inner tube 42 and along the first lumen 36 and into the punctured vein. In this way, the wire member 62 is fed in a single operation into the vein without requiring any manipulation of the syringe 10 and needle 20 within the vein and thereby reducing patient discomfort, trauma to the vein, the possibility of movement of the distal end of the needle 20 from the initial puncture site. Once the tip 63 of wire member 62 is appropriately positioned extending into the vein, beyond the distal tip of the needle 20, the needle 20 is withdrawn leaving member 62 in the vein. If necessary, the physician can press gently upon the end 63 of the guidewire member 62 extending beyond the distal tip of the needle 20 in the vein to hold that tip 63 in position while withdrawing the needle 20 from the vein. A catheter tube 74 can then be slid over the wire member 62 and into the vein at the puncture site.

Needle 20 can be customized for left-handed doctors by having the side passageway project outwardly from the left side of the axial passageway looking down on the needle from its mounting end with the bevel 48 again facing up.

FIGS. 3 and 4 show two flexible wire members 62 and 62' being fed through the needle 20 of FIGS. 1–2. The second wire member 62' is fed through the axial passageway 28 through the enlarged tapered opening 66 and a second, more severely tapered portion 70 of that passageway, along the passageway 28 and between the second, outer tube 44 defining the shank of needle 20 and the first, inner tube 42 carrying the first flexible wire member 62. If the first, inner tube 42 is made of a flexible material, it can displace in the axial passageway and the outer tube 44 to more easily accommodate the second flexible wire member 62'.

FIG. 5 is a longitudinal cross-section of a second embodiment needle of the present invention indicated generally at 120. Needle 120 differs from needle 20 in FIGS. 1–4 only in that the second, outer tube 144 of needle 120 extends from the distal end 126 of the main, axial passageway 28 past the junction 32 of the side passageway 30 with axial passageway 28. A notch 145 is provided at the distal end 144a of second tube 144 to permit first tube to branch into the side passageway 30.

FIG. 6 depicts an alternate proximal end 244a of an alternate second outer tube 244, which might be used in place of tube 144 in needle 120. A notch 245 is provided along the sidewall of tube 244 and the unbroken distal end 244a of tube 244 is continued past junction 32 towards the mounting end 24 of needle 120.

FIG. 7 depicts in an exploded view, an adapter indicated generally at 318, which includes a hub 322 substantially similar to hub 22 and a first, preferably flexible tube 42 extending from a side passageway 30 of hub 322 through junction 32 and the portion of 28b of the main axial passageway between junction 32 and a distal end 326 of the hub 322. Adapter 318 differs from needle 20 in that instead of a second, outer tube 44, which defines the shank of needle 20, adapter 318 is provided with a Luer-type mating connector 382 in the form of a conventional Luer-type receiver, which receives the mounting end 384 of a standard single lumen needle 386 having a radially protruding, releasably matable connector in the form of Luer-type diametrically opposed, radially outwardly projecting dogs 389 and a shank 421. Thus, the distal end 326 and mounting end 324 of hub 322 have connectors 382 and 369 which would be releasably matable with one another could the dogs 389 at the mounting end 324 be installed into the Luer receiver matable connector 328 at the distal end 326. The provision of the standard releasably matable, Luer connectors 382 and 369 permit adapter 318 to be releasably mated between a conventional single lumen needle 386 and syringe 10 combination having Luer-type releasable matable connectors 316 and 389 similar to the connectors 382 and 369 of hub 322.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A double lumen introducing needle comprising:

a hub having a mounting end and an distal end opposing the mounting end, an at least substantially straight axial passageway extending through the hub between the mounting and distal ends and a side passageway branching from a junction with the axial passageway in the hub and extending away from the junction and the distal end of the hub at an acute angle to the axial passageway extending from the junction to the mounting end, the side passageway terminating in a separate, side port of the hub;

a first lumen extending continuously and unbrokenly from the side passageway, through the junction, along the main passageway between the junction and the distal end of the hub and projecting outwardly from the distal end of the hub, the first lumen having a proximal end located within the hub and fluidly isolated from the axial passageway; and sidewalls of the hub defining the axial passageway surrounding a second lumen, the second lumen extending between the mounting end and distal end of the hub and surrounding the first lumen within the axial passageway.

2. The needle of claim 1 wherein the first open end of the first lumen is located in the side passageway and wherein the first open end of the first lumen is fluidly isolated from the axial passageway.

3. The needle of claim 1 further comprising:

an inner tube extending continuously and unbrokenly from the side passageway, through the junction, along the main passageway between the junction and the distal end of the hub and projecting outwardly from the distal end of the hub, a hollow interior of the inner tube defining the first lumen of the needle.

4. The needle of claim 3 further comprising:

an outer tube, separate from the inner tube, extending from the distal end of the axial passageway away from the hub and entirely around the inner tube extending from the hub, a hollow interior of the outer tube defining at least a portion of the second lumen surrounding the inner tube and the first lumen, the outer tube being fluidly coupled with the mounting end of the hub through the axial passageway.

5. The needle of claim 4 wherein the outer tube is more rigid than the inner tube.

6. The needle of claim 4 wherein the second tube has a free distal end with a bevel defining a point and wherein the inner tube has a distal free end terminating at the bevel.

7. The needle of claim 4 wherein the outer tube is a single lumen needle releasably attached to the distal end of the hub.

8. The needle of claim 3 wherein the distal end and the mounting end of the hub are configured as connectors releasably matable with one another whereby the hub can be releasably mated with a releasable mated single lumen needle and syringe combination having releasably matable connectors similar to the releasably matable connectors of the hub.

9. The needle of claim 3 wherein an outer tubular wall of the inner tube is sealed with the side passageway to fluidly isolate the first open end of the first lumen from the axial passageway.

10. The needle of claim 1 further comprising a closure on a side port end of the side passageway.

11. The combination of claim 10 wherein the closure comprises a plug in a side port end of the side passageway, the plug having a preformed slit opening.

12. The needle of claim 10 in further combination with a flexible wire member having a leading end inserted through an opening in the closure and into the first lumen at the side port.

13. The needle of claim 12 wherein the first flexible wire member is a cardiac lead having a leading end with an exposed electrode extending into the first lumen along the side passageway.

14. The needle of claim 13 further comprising a tetrafluoroethylene catheter around the second outer tube.

15. The needle of claim 12 in further combination with a second flexible wire member extended through the axial passageway.

16. The needle of claim 12 wherein the flexible wire member is a guidewire.

17. The needle of claim 1 wherein the axial passageway terminates at the mounting end of the hub in an enlarged, tapered opening.

18. The needle of claim 1 further comprising an external Luer connection flange projecting radially outwardly on the mounting end of the hub.

19. The needle of claim 1 in combination with syringe barrel attached to the mounting end of the hub and fluidly coupled with the axial passageway.

20. A double lumen introducing needle comprising a hub with a main body portion having a mounting end and a distal end opposing the mounting end, a needle shank projecting from the distal end of the hub, a syringe connector located at the mounting end, an axial passageway extending entirely through the main body portion of the hub between the mounting end and the distal end, a sidearm portion of the hub branching from the main body portion of the hub between the distal end and the mounting end, a side passageway in the sidearm portion branching from a junction with the axial passageway in the main body portion, and a first, inner lumen having a termination in the side passageway, the first, inner lumen being formed at least in part by a first tube having a circumferential outer tubular wall which is circumferentially surrounded by and sealed with the side passageway, and the axial passageway defining at least part of a second, outer lumen of the needle extending at least continuously through the hub between the distal end and the mounting end of the hub.

21. The double lumen introducing needle of claim 20 in combination with a flexible wire member passed through the first, inner lumen and the first tube and along the axial passageway from the junction towards the distal end and into the needle shank.

22. A double lumen introducing needle comprising a hub with a main body portion having a mounting end and a distal end opposing the mounting end, a needle shank projecting from the distal end of the hub, a syringe connector located at the mounting end, an axial passageway extending entirely through the main body portion of the hub between the mounting end and the distal end, a sidearm portion of the hub branching from the main body portion of the hub between the distal end and the mounting end, a side passageway in the sidearm portion branching from a junction with the axial passageway in the main body portion, the side passageway terminating in an open port, and a closure sealingly plugged into the open port, the closure having a restricted opening therethrough sized for passage of at least a flexible wire member in the form of one of a guide wire and a cardiac lead.

23. The double lumen introducing needle of claim 22 in combination with a flexible wire member in the form of one of a guide wire and a cardiac lead passed through the restricted opening of the closure, along the side passageway and the axial passageway from the junction through the distal end and into the needle shank.

24. A double lumen introducing needle comprising a hub with a main body portion having a mounting end and a distal end opposing the mounting end, a needle shank projecting from the distal end of the hub, a syringe connector located at the mounting end, an axial passageway extending entirely through the main body portion of the hub between the mounting end and the distal end, a sidearm portion of the hub branching from the main body portion of the hub between the distal end and the mounting end, a side passageway in the sidearm portion branching from a junction with the axial passageway in the main body portion, the side passageway terminating an open port, and a cap sealingly secured over the open port, the cap having an opening therethrough sized for passage of at least a flexible wire member in the form of one of a guide wire and cardiac lead.

25. The double lumen introducing needle of claim 24 in combination with a flexible wire member in the form of one of a guide wire and a cardiac lead passed through the opening of the cap, and along the side passageway and the axial passageway from the junction though the distal end and into the needle shank.

* * * * *